United States Patent
Bara (10) Patent No.: US 10,350,544 B2
(45) Date of Patent: *Jul. 16, 2019

(54) GAS TREATING SOLUTIONS CONTAINING IMIDAZOLE-AMINE COMPOUNDS

(71) Applicant: THE BOARD OF TRUSTEES OF THE UNIVERSITY OF ALABAMA, Tuscaloosa, AL (US)

(72) Inventor: Jason Edward Bara, Tuscaloosa, AL (US)

(73) Assignee: THE BOARD OF TRUSTEES OF THE UNIVERSITY OF ALABAMA, Tuscaloosa, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,961

(22) PCT Filed: Feb. 4, 2016

(86) PCT No.: PCT/US2016/016591
§ 371 (c)(1),
(2) Date: Aug. 1, 2017

(87) PCT Pub. No.: WO2016/126957
PCT Pub. Date: Aug. 11, 2016

(65) Prior Publication Data
US 2018/0021723 A1    Jan. 25, 2018

Related U.S. Application Data

(60) Provisional application No. 62/111,896, filed on Feb. 4, 2015.

(51) Int. Cl.
B01D 53/78    (2006.01)
C07D 233/61   (2006.01)
(Continued)

(52) U.S. Cl.
CPC .......... B01D 53/62 (2013.01); C07D 233/61 (2013.01); *B01D 2252/20473* (2013.01);
(Continued)

(58) Field of Classification Search
None
See application file for complete search history.

(56) References Cited

U.S. PATENT DOCUMENTS

| | | | |
|---|---|---|---|
| 4,088,735 A | 5/1978 | Bratzler et al. | |
| 4,624,838 A | 11/1986 | Pan et al. | |

(Continued)

FOREIGN PATENT DOCUMENTS

| | | |
|---|---|---|
| CN | 100999498 A | 7/2007 |
| GB | 1483038 A | 8/1977 |

(Continued)

OTHER PUBLICATIONS

Online catalog page for "3-(2-methyl-1H-innidazol-1-yl)propan-1-amine." BetaPharma Co., Ltd. (2005). Viewed Jun. 18, 20018 at http://www.betapharma.cn/products_list.php?searchstr=2258-21-1&inway=CAS&Input.x=39&Input.y=2.*

(Continued)

*Primary Examiner* — Daniel Berns
(74) *Attorney, Agent, or Firm* — Meunier Carlin & Curfman LLC (57) ABSTRACT

Systems comprising a composition where an imidazole is tethered to an amine and a solvent are described herein. Methods of their preparation and use are also described herein. The methods of using the systems include the reduction of volatile compounds from gas streams and liquid stream.

20 Claims, 4 Drawing Sheets

(51) Int. Cl.
| | |
|---|---|
| *B01D 53/44* | (2006.01) |
| *B01D 53/48* | (2006.01) |
| *B01D 53/50* | (2006.01) |
| *B01D 53/52* | (2006.01) |
| *B01D 53/56* | (2006.01) |
| *B01D 53/60* | (2006.01) |
| *B01D 53/62* | (2006.01) |

(52) U.S. Cl.
CPC .... *B01D 2252/50* (2013.01); *B01D 2252/502* (2013.01); *B01D 2257/504* (2013.01); *Y02C 10/04* (2013.01); *Y02P 20/152* (2015.11)

(56) References Cited

U.S. PATENT DOCUMENTS

| | | | |
|---|---|---|---|
| 4,775,519 | A | 10/1988 | Yit Nieh |
| 5,547,972 | A | 8/1996 | Clegg et al. |
| 7,744,838 | B2 | 6/2010 | Davis, Jr. |
| 8,506,914 | B2 | 8/2013 | Bara |
| 2005/0010076 | A1 | 1/2005 | Wasserscheid et al. |
| 2005/0129598 | A1 | 6/2005 | Chinn et al. |
| 2007/0044658 | A1 | 3/2007 | Rochelle et al. |
| 2007/0286783 | A1 | 12/2007 | Carrette et al. |
| 2009/0291872 | A1 | 11/2009 | Bara et al. |
| 2009/0291874 | A1 | 11/2009 | Bara et al. |
| 2010/0326276 | A1 | 12/2010 | Blair et al. |
| 2011/0223087 | A1 | 9/2011 | Lustig et al. |
| 2011/0256043 | A1 | 10/2011 | Blair et al. |
| 2012/0248372 | A1 | 10/2012 | Bara |
| 2012/0294785 | A1 | 11/2012 | Murai et al. |
| 2013/0143939 | A1 | 6/2013 | Bara |

FOREIGN PATENT DOCUMENTS

| | | | |
|---|---|---|---|
| GB | 2079307 | A | 1/1982 |
| GB | 2167397 | A | 5/1986 |
| JP | 2011025100 | A | 2/2011 |
| PL | 127211 | B2 | 10/1983 |
| RU | 2008146745 | A | 6/2010 |
| WO | 2012135178 | A1 | 10/2012 |

OTHER PUBLICATIONS

"Safety Data Sheet, 4-Imidazol-1-yl-butylamine." Oakwood Products, Inc., Mar. 27, 2012. Viewed Oct. 25, 2018 at http://www.oakwoodchemical.com/ShowMSDS.aspx?Number=058552.*
International Search Report and Written Opinion dated Apr. 14, 2016, in the International Application No. PCT/US2016/016591.
International Preliminary Report on Patentability for PCT/US2012/030672 dated Oct. 10, 2013.
International Search Report for PCT/US2012/030672 dated Sep. 12, 2012.
Non-Final Office Action for U.S. Appl. No. 13/430,813 dated Feb. 8, 2013.
Non-Final Office Action for U.S. Appl. No. 13/913,616 dated Dec. 9, 2013.
Notice of Allowance for U.S. Appl. No. 13/430,813 dated May 16, 2013.
Notice of Allowance for U.S. Appl. No. 13/913,616 dated Apr. 14, 2014.
Office Action dated Apr. 8, 2016 for European Application No. 12763371.7.
Bara, Jason E. et al., "Room-Temperature Ionic Liquids and Composite Materials: Platform Technologies for CO2 Capture", Accounts of Chemical Research, vol. 43, No. 1, ISSN 0001-4842, 2010.
Blanchard, et al., "High-Pressure Phase Behavior of Ionic Liquid/CO2 Systems", J. Phys. Chem., 105, 2001, 2437-2444.
Camper, et al., "Room-Temperature Ionic Liquid-Amine Solutions: Tunable Solvents for Efficient and Reversible Capture of CO2", Ind. Eng. Chem. Res., 47, 2008, 8496-8498.
First Office Action for Application No. CN201280025608.9, dated Oct. 31, 2014.
Office Action for Application No. NZ615884 dated Jun. 9, 2014.
Shannon, et al., "Evaluation of Alkylimidazoles as Physical Solvents for CO2/CH4 Separation", Ind. Eng. Chem. Res, 51, 2012, 515-522.
Shannon, Matthew S. et al., "Properties of Alkylimidazoles as Solvents for CO2 Capture and Comparisons to Imidazolium-Based Ionic Liquids", Industrial and Engineering Chemistry Research, 50, 2011, 8665-8677.
Shannon, Matthew S. et al., "Reactive and Reversible Ionic Liquids for CO2 Capture and Acid Gas Removal", Separation Science and Technology, 47.
Sharma, Amit et al., "Mass Transfer and Solubility of CO and H2 in Ionic Liquid. Case of [Bmim][PF6] with Gas-Inducing Stirrer Reactor", Industrial and Engineering Chemistry Research, vol. 48, No. 8, Mar. 23, 2009, 4075-4082.
Smith, Grant D. et al., "A Comparison of Ether- and Alkyl-Derivatized Imidazolium-Based Room-Temperature Ionic Liquids: a Molecular Dynamics Simulation Study", Physical Chemistry Chemical Physics, 10(4), 2008.
Smith, Grant D. et al., "A Comparison of Fluoroalkyl-derivatized Imidazolium: TFSI and Alkyl-derivatized imidazolium: TFSI Ionic Liquids: a Molecular Dynamics Simulation Study", Physical Chemistry Chemical Physics, 12(26), 2010.
Strazisar, Brian R. et al., "Degradation Pathways for Monoethanolamine in a CO2 Capture Facility", Energy & Fuels, 17, 2003, 1034-1039.
Tokuda, Hiroyuki et al., "Physicochemical Properties and Structures of Room Temperature Ionic Liquids. 3. Variation of Alkyl Chain Length in Imidazolium Cation", Journal of Physical Chemistry B, 109, 2005, 6103-6110.
Supplemental European Search Report for Application No. 12763371.7 dated Jul. 29, 2014.

* cited by examiner

GAS TREATING SOLUTIONS CONTAINING IMIDAZOLE-AMINE COMPOUNDS

CROSS REFERENCE TO RELATED APPLICATIONS

This application is a 371 of international application no. PCT/US2016/016591, entitled "Gas Treating Solutions Containing Imidazole-Amine Compounds," filed Feb. 4, 2016, which claims priority to U.S. Provisional Application No. 62/111,896, filed Feb. 4, 2015, the contents of which are herein incorporated by reference in their entireties.

STATEMENT REGARDING FEDERALLY SPONSORED RESEARCH

This invention was made with government support under grant number DE-FE0013303 awarded by the Department of Energy. The government has certain rights in the invention.

FIELD

The subject matter disclosed herein generally relates to systems comprising an imidazole tethered to an amine and a solvent. Also, the subject matter described herein generally relates to methods of using the systems described herein to capture and reduce volatile compounds from gas streams and liquid streams.

BACKGROUND

There is a worldwide interest in capturing and sequestering or reusing carbon dioxide ($CO_2$) emissions to stabilize the climate. Aqueous amine processes, widely used throughout the natural gas industry to reduce $CO_2$ from gas streams via chemical reaction, represent the benchmark by which $CO_2$ capture technologies are evaluated (NETL, *Carbon Sequestration Technology Roadmap and Program Plan* (2007); Rochelle, G. T., "Amine Scrubbing for $CO_2$ Capture," *Science*, 325:1652-1654 (2009)). While effective at reducing $CO_2$ from gas streams, amine processes are highly energy intensive, with much of the energy penalty attributed to boiling water during amine regeneration. Thus, aqueous amine processes will inherently suffer from large energy penalties. However, new solvents with little or no volatility can provide the desired energy efficiency.

Aqueous amines processes can suffer due to the relatively high vapor pressure of the amine compounds. Additionally, many of the amines utilized for carbon capture might not be cost effective. Other strategies, such as the use of N-functionalized imidazoles (see Bara, J. E., WO 2012135178 A1, (2011)) or imido-acid salts (see Bara, J. E., U.S. Publication No. US 20130143939 A1 (2011)), have been previously suggested for $CO_2$ capture and storage.

What are still needed are new systems for capturing $CO_2$ and other volatile compounds. The compounds and methods disclosed herein address these needs.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions. In a further aspect, the disclosed subject matter relates to systems that can be used for the capture of volatile compounds in industrial and commercial natural gas production and power generation industries. More specifically, systems for the reduction of volatile compounds are described herein. The systems comprise compositions where imidazole is tethered to an amine and a solvent. The imidazole tethered to an amine for use in the disclosed system is non-ionic under neutral conditions (e.g., under conditions where an acidic proton is not available). In other examples, the imidazole tethered to an amine is not functionalized on both nitrogen atoms.

Further provided herein are methods for reducing volatile compounds, e.g., $CO_2$, $SO_2$, $H_2S$, and others disclosed herein, from a stream (e.g., a gas stream or a liquid stream). The methods include contacting the stream with an effective amount of a system comprising a composition where an imidazole is tethered to an amine and a solvent, wherein the imidazole tethered to an amine is non-ionic under neutral conditions.

Methods for sweetening a natural gas feed stream are also provided herein. The methods comprise contacting the natural gas feed stream with an effective amount of a system as described herein to form a purified natural gas feed stream and a gas rich system and separating the purified natural gas feed stream from the gas-rich system. The methods can further comprise regenerating the system by, for example, heating or pressurizing the gas rich system.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 5 is a graph of $CO_2$ uptake as a function of pressure for solutions containing 4-methyl-aminopropyl imidazole (4-methyl); 2-methyl-aminopropyl imidazole (2-methyl);

2-ethyl aminopropyl imidazole (2-ethyl); 2-ethyl-4-methyl aminopropyl imidazole (2-ethyl-4-methyl), and 1-(3-aminopropyl)imidazole, at 60° C.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

By "reduce" or other forms of the word, such as "reducing" or "reduction," is meant lowering of an event or characteristic (e.g., volatile compounds in a stream). It is understood that this is typically in relation to some standard or expected value, in other words it is relative, but that it is not always necessary for the standard or relative value to be referred to. For example, "reduces $CO_2$" means reducing the amount of $CO_2$ in a stream relative to a standard or a control. As used herein, reduce can include complete removal. In the disclosed method, reduction can refer to a 10%, 20%, 30%, 40%, 50%, 60%, 70%, 80%, 90%, or 100% decrease as compared to the standard or a control. It is understood that the terms "sequester," "capture," "remove," and "separation" are used synonymously with the term "reduce."

By "treat" or other forms of the word, such as "treated" or "treatment," is meant to add or mix two or more compounds, compositions, or materials under appropriate conditions to produce a desired product or effect (e.g., to reduce or eliminate a particular characteristic or event such as $CO_2$ reduction). The terms "contact" and "react" are used synonymously with the term "treat."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "non-ionic" as used herein refers to being free of ionic groups or groups that are readily substantially ionized in water. A "non-ionic" compound does not contain a charge at neutral pH (e.g., at a pH from 6.7 to 7.3). However, non-ionic compounds can be made to have a charge under acidic or basic conditions or by methods known in the art, e.g., protonation, deprotonation, oxidation, reduction, alkylation, acetylation, esterification, deesterification, hydrolysis, etc. Thus, the disclosed "non-ionic" compounds can become ionic under conditions where, for example, an acidic proton is available to protonate the compound.

The term "volatile compound" as used herein refers to chemical compounds that are capable of vaporizing to a significant amount or that exist as a gas at ambient conditions. The "volatile compounds" described herein are found in the streams and have higher vapor pressures than the stream, such as natural gas feeds. Examples of volatile compounds include light gases and acid gases, such as $CO_2$, $O_2$, $N_2$, $CH_4$, $H_2$, hydrocarbons, $H_2S$, $SO_2$, $NO$, $NO_2$, $COS$, $CS_2$, and the like.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl groups can be substituted or unsubstituted. The aryl and heteroaryl groups can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The term "amino" as used herein is represented by the formula —NA$^1$A$^2$, where A$^1$ and A$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiA$^1$A$^2$A$^3$, where A$^1$, A$^2$, and A$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound can, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Imidazole Tethered to an Amine

Systems comprising a composition where imidazole is tethered to an amine are provided herein. These compositions are useful for reducing volatile compounds, such as carbon dioxide ($CO_2$), carbon monoxide (CO), sulfur dioxide ($SO_2$), hydrogen sulfide ($H_2S$), nitrogen oxide (NO), nitrogen dioxide ($NO_2$), carbonyl sulfide (COS), and carbon disulfide ($CS_2$), mercaptans, $H_2O$, $O_2$, $H_2$, $N_2$, $C_1$-$C_8$ hydrocarbons (e.g., methane and propane), volatile organic compounds, and mixtures of these and other volatile compounds from gas streams and liquid streams. The imidazole tethered to an amine are non-ionic compounds under neutral compounds (i.e., the imidazoles do not contain a charge under neutral conditions). Neutral conditions include conditions where no proton is available to react with the imidazole tethered to an amine (i.e., to protonate the imidazole tethered to an amine). Protons can be present, but the conditions of the system, including the basicity of the imidazole tethered to an amine, are such that no significant amount of protonation of the imidazole tethered to an amine occurs, i.e., the conditions do not produce imidazolium ion. Neutral conditions for the imidazole tethered to an amine include conditions where the pH of the system is from about 6.7 to about 7.3. In some examples, the pH of the system can be about 6.7, about 6.8, about 6.9, about 7.0, about 7.1, about 7.2, about 7.3, or the like, where any of the stated values can form an upper or lower endpoint of a range. The term "neutral conditions" is used herein relative to the specific imidazole, thus this term means conditions wherein the imidazole is not protonated (i.e., made cationic). For example, the pH of the system can be from about 6.8 to about 7.2, or from about 6.9 to about 7.1. Further, the imidazole tethered to an amine described herein are not components of an ionic-liquid (i.e., liquids that contain ions under all conditions).

The imidazole tethered to an amine can comprise three components: (1) the imidazole, (2) the tether, and (3) the amine as depicted by Formula I.

Formula I

The imidazole tethered to an amine can comprise an imidazole that can be substituted as in Formula I. Also in Formula I, X, Y, and Z can be each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, substituted or unsubstituted aryloxyl, substituted or unsubstituted amino, cyano, or nitro.

Further in Formula I, adjacent groups, i.e., Y and Z, X and Y, and X and Z, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. X, Y, and Z can each also be halides, cyano, nitro, and other similar groups.

The tether, R, can be substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, or substituted or unsubstituted aryloxyl.

X, Y, Z, and R can be independently substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides. In specific examples, X, Y, and Z can all be H. In other specific examples, at least one of X, Y, and Z is unsubstituted $C_{1-4}$ alkyl, e.g., methyl.

Formula II

In some embodiments, the tether can specifically be a substituted or unsubstituted $C_{1-20}$ alkyl as represented by Formula II. In Formula II, n is an integer from 1 to 20. The tether can be R can be substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides.

The imidazole tethered to an amine can comprise an imidazole that can be substituted as in Formula II. Also in Formula II, X, Y, and Z are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, substituted or unsubstituted aryloxyl, substituted or unsubstituted amino, cyano, or nitro.

Further in Formula II, adjacent groups, i.e., Y and Z, X and Y, and X and Z, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. X, Y, and Z can each also be halides, cyano, nitro, and other similar groups.

X, Y, and Z can be independently substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides. In specific examples, X, Y, and Z can all be H. In other specific examples, at least one of X, Y, and Z is unsubstituted $C_{1-4}$ alkyl, e.g., methyl.

Formula III

In some embodiments, the tether can specifically be a substituted or unsubstitued polyether bridge as represented by Formula III. In Formula III, n is an integer from 1 to 20. The tether can be R can be substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides.

The imidazole tethered to an amine can comprise an imidazole that can be substituted as in Formula III. Also in Formula III, X, Y, and Z are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, substituted or unsubstituted aryloxyl, substituted or unsubstituted amino, cyano, or nitro.

Further in Formula III, adjacent groups, i.e., Y and Z, X and Y, and X and Z, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. X, Y, and Z can each also be halides, cyano, nitro, and other similar groups.

X, Y, and Z can be independently substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides. In specific examples, X, Y, and Z can all be H. In other specific examples, at least one of X, Y, and Z is unsubstituted $C_{1-4}$ alkyl, e.g., methyl.

Formula IV

In some embodiments the amine can be substituted. The amine can be a primary amine, secondary amine, tertiary amine, or a cyclic amine as in Formula IV. $R^1$ and $R^2$ can each independently be selected from the group consisting of hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, or substituted or unsubstituted aryloxyl.

In some embodiments, the amine can be a primary amine. According to these examples $R^1$ and $R^2$ are hydrogen according to Formula IV.

The imidazole tethered to an amine can then comprise an imidazole that can be substituted as in Formula IV. Also in Formula IV, X, Y, and Z are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, substituted or unsubstituted aryloxyl, substituted or unsubstituted amino, cyano, or nitro.

Further in Formula IV, adjacent groups, i.e., Y and Z, X and Y, and X and Z, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substi- tuted or unsubstituted heterocycloalkynyl. X, Y, and Z can each also be halides, cyano, nitro, and other similar groups. In specific examples, X, Y, and Z can all be H. In other specific examples, at least one of X, Y, and Z is unsubstituted $C_{1-4}$ alkyl, e.g., methyl.

The tether, R, can be substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, or substituted or unsubstituted aryloxyl.

X, Y, Z, R, $R^1$, and $R^2$ can be independently substituted with $C_{1-20}$ alkyl, $C_{2-20}$ alkenyl, $C_{2-20}$ alkynyl, $C_{1-20}$ heteroalkyl, $C_{2-20}$ heteroalkenyl, $C_{2-20}$ heteroalkynyl, cycloalkyl, heterocycloalkyl, aryl, heteroaryl, thiol, alkoxyl, aryloxyl, hydroxyl, cyano, amino, halides, nitro, or sulfides.

Particular examples of Formula IV include where R is unsubstituted $C_{1-6}$ alkyl, $C_{1-6}$ alkyl substituted with one or more $C_{1-4}$ alkyl groups, or $(C_{1-4}$ alkoxyl$)_n$, where n is 1-6. Other examples of Formula IV include where X is methyl. Other examples of Formula IV include where $R^1$ is H and $R^2$ is $C_{1-4}$ alkyl.

Particular examples of Formula IV include the following compounds:

Formula IV-A

Formula IV-B

Formula IV-C

Formula IV-D

Solvent

The system can also comprise a solvent or a mixture of solvents. Solvents, such as water, tetrahydrofuran (THF), dichloromethane, acetonitrile, toluene, dimethyl sulfoxide (DMSO), pyridine, dimethylformamide, dioxane, glycol solvents, methanol, ethanol, propanol, butanol, ethyl acetate, methyl ethyl ketone, acetone, and the like, can be added to the imidazole tethered to an amine to provide a system to capture gases. In a preferred aspect, the solvent is water.

System

The systems disclosed herein can contain a composition where an imidazole is tethered to an amine, such as any compound having a formula as in Formula I-IV, and a solvent (preferably water). The systems described herein are not ionic liquids. For example, the combination of an imidazole tethered to an amine does not result in a low melting salt. Upon addition of an acidic gas (e.g., $CO_2$, $H_2S$, etc.) the system can contain charge. Further, the systems described herein can be distilled whereas ionic liquids do not have this capability. The systems disclosed herein can be neat (i.e., can be composed of the imidazole tethered to an amine without any additional solvent) or can be dissolved or dispersed in one or more additional solvents. In some embodiments, the system is a neat system comprised primarily of an imidazole tethered to an amine. Systems comprised primarily of the imidazole tethered to an amine can contain about 3 wt. % or less of impurities (i.e., the system contains about 97 wt. % or higher, about 98 wt. % or higher, or about 99 wt. % or higher imidazole tethered to an amine based on the weight of the system).

In some embodiments, the system is a neat system composed of a mixture of an imidazole tethered to an amine. The system can have low volatility, low viscosity, and high $CO_2$ capacity. The properties of the system can be altered by percentage of the imidazole tethered to an amine in a solvent.

The imidazole tethered to an amine can comprise 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% by weight of the system, where any of the stated values can form an upper or lower endpoint of a range. In further examples, the imidazole tethered to an amine can comprise from 1% to 99%, 10% to 90%, 20% to 80%, 30% to 70%, 40% to 60%, or 50% by weight of the system. For example, the imidazole tethered to an amine can comprise 40% of the system. In other examples, the imidazole tethered to an amine can comprise 60% of the system.

The systems described herein are substantially free from amines, not tethered to an imidazole (e.g., free amines). By substantially free is meant that free amines are present at less than about 3%, 2%, 1%, 0.9%, 0.8%, 0.7%, 0.6%, 0.5%, 0.4%, 0.3%, 0.2%, 0.1%, 0.001%, 0.0001% by weight of the system.

As described above, the systems described herein can be dissolved or dispersed in one or more additional solvents. For example, the imidazole tethered to an amine can be mixed with a solvent such as water, tetrahydrofuran (THF), dichloromethane, acetonitrile, toluene, dimethyl sulfoxide (DMSO), pyridine, dimethylformamide, dioxane, glycol solvents, methanol, ethanol, propanol, butanol, ethyl acetate, methyl ethyl ketone, acetone, and the like to provide a system. In these examples, the imidazole tethered to an amine can comprise from about 0.1% to about 99.9% of the system. For example, the imidazole tethered to an amine can comprise from about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% by weight of the system, where any of the stated values can form an upper or lower endpoint of a range. In further examples, the imidazole tethered to an amine can comprise from 1% to 99%, 10% to 90%, 20% to 80%, 30% to 70%, 40% to 60%, or 50% by weight of the system.

The systems described herein are substantially free from volatile organic compounds. By substantially free is meant that volatile organic compounds are present at less than about 3%, 2%, 1%, 0.9%, 0.8%, 0.7%, 0.6%, 0.5%, 0.4%, 0.3%, 0.2%, 0.1%, 0.001%, or 0.0001% by weight of the system.

Methods of Using the Systems

The systems disclosed herein disclosed herein can be used to capture volatile compounds from a stream. The systems make use of a composition where an imidazole is tethered to an amine. By tethering an amine functional group to an imidazole through a covalent bond, the vapor pressure of the amine can be lowered. Additionally, these compounds can be prepared with commodity chemicals, which can result in lower system costs.

The methods for reducing volatile compounds from streams (e.g., gas streams or liquid streams) can be similar to those described in Bara et al. U.S. Published Patent No. 20090291874 A1, which is incorporated by reference herein for its methods and techniques of volatile compound reduction. As used herein, volatile compounds can include to undesirable gaseous components found in a source and having a molecular weight lower than 150 g/mol. For example, the volatile compounds can have a molecular weight lower than 140 g/mol, 130 g/mol, 120 g/mol, 110 g/mol, 100 g/mol, 90 g/mol, 80 g/mol, 70 g/mol, 60 g/mol, 50 g/mol, 40 g/mol, 30 g/mol, 20 g/mol, or the like, where any of the stated values can form an upper or lower endpoint of a range. Examples of volatile compounds include $CO_2$, CO, COS, $H_2S$, $SO_2$, NO, $N_2O$, mercaptans, $H_2O$, $O_2$, $H_2$, $N_2$, $C_1$-$C_8$ hydrocarbons (e.g., methane and propane), volatile organic compounds, and mixtures of these.

The method for reducing a volatile compound from a stream can include contacting the stream with an effective amount of a system as described herein. In some embodiments, the system comprises an imidazole tethered to an amine and a solvent. For example, volatile compounds from a gas stream (e.g., a natural gas stream or a flue gas stream) can be reduced according to this method.

Further described herein is a method for sweetening a natural gas feed stream. The method includes contacting the natural gas feed stream with an effective amount of a system as described herein to form a purified natural gas feed stream and a gas-rich system. Optionally, the natural gas feed stream can be contacted with a second system as described herein. The contacting of the natural gas feed stream with the second system can be performed simultaneously as the contacting with the first system (i.e., the gas feed stream can be contacted with both the first and second system) or can be performed sequentially (i.e., the gas feed stream can be contacted with the second system after the gas feed stream has been contacted with the first system). The purified natural gas feed stream can then be separated from the gas-rich system. In some embodiments, the volatile compounds are reduced from the gas-rich system to regenerate the system. The system can be regenerated by heating or pressurizing the gas-rich system.

The examples below are intended to further illustrate certain aspects of the methods and compositions described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1

Synthesis of N-propylamine-2-methyl-imidazole 2-methyl-imidazole is reacted with a molar equivalent of acrylonitrile in a mixture of triethylamine and toluene. The mixture is heated at 50° C. to generate an intermediate imidazole compound linked to acrylonitrile, N-propanenitrile-2-methyl-imidazole. The nitrile bond is reduced by bubbling hydrogen gas into a solution of N-propanenitrile-2-methyl-imidazole in methanol catalyzed by Rainey Nickel. N-propylamine-2-imidazole is generated from the reduction reaction as seen in Scheme I.

Scheme I

Example 2

Generic Synthesis of an Imidazole Tethered to an Amine Using a Protecting Group

Any R group for the tether can be integrated by using a generic imide protecting group. For example, potassium 1,3-dioxoisoindolin-2-ide can be reacted with an alkylating agent as seen in Scheme II to generate a tethering group that is protected by 1,3-dioxoisoindolin-2-ide.

Scheme II

The protected tethering group is then reacted with a selected imidazole, for example 2-methyl-imidazole with sodium hydride in THF. Sodium hydride will deprotonated 2-methyl-imidazole and allow the tether to react with the nitrogen atom on the imidazole as seen in Scheme III.

Scheme III

The protecting group can be removed by reducing the imide with hydrazine in ethanol. The solution is heated at 60° C. for 16 h as seen in Scheme IV.

Scheme IV

Example 3

$CO_2$ Uptake

Four solutions containing the amine-functionalized imidazoles, 4-methyl-aminopropyl imidazole; 2-methyl-aminopropyl imidazole; 2-ethyl aminopropyl imidazole; and 2-ethyl-4-methyl aminopropyl imidazole, were prepared. The amine-functionalized imidazoles were each mixed with water in a glass vial at a concentration of 3 mol/L. The vials were sealed and the liquids were held on a vibrating mixer until a homogeneous solution was achieved. A solution containing 1-(3-aminopropyl)imidazole was also prepared using a similar method as described for preparing the amine-functionalized imidazoles.

Figure 1:
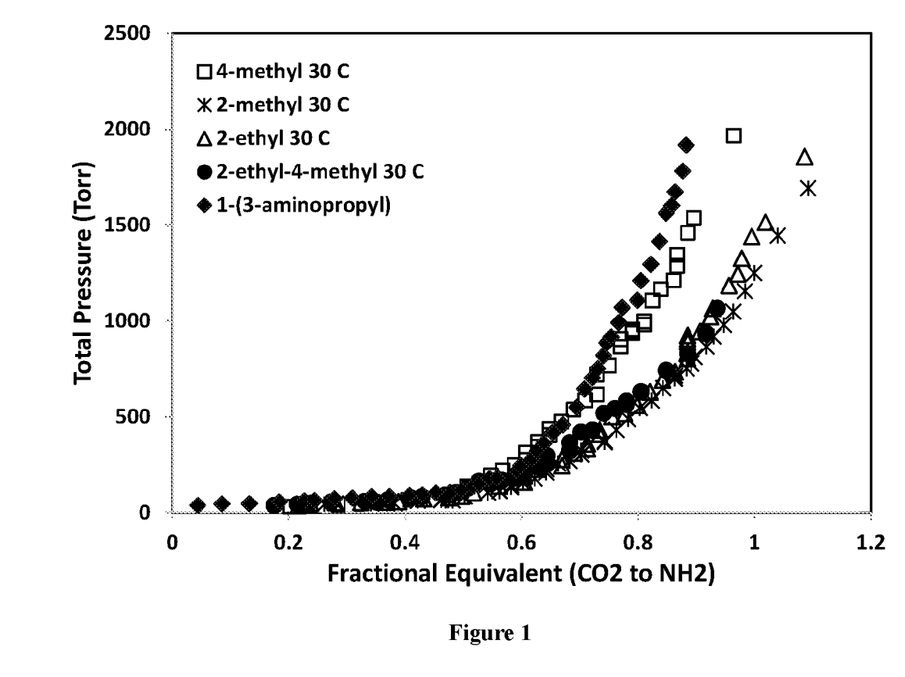
FIG. 1 is a graph of $CO_2$ uptake as a function of total pressure, for solutions containing 4-methyl-aminopropyl imidazole (4-methyl); 2-methyl-aminopropyl imidazole (2-methyl); 2-ethyl aminopropyl imidazole (2-ethyl); 2-ethyl-4-methyl aminopropyl imidazole (2-ethyl-4-methyl) compared to 1-(3-aminopropyl)imidazole, at 30° C.
Figure 2:
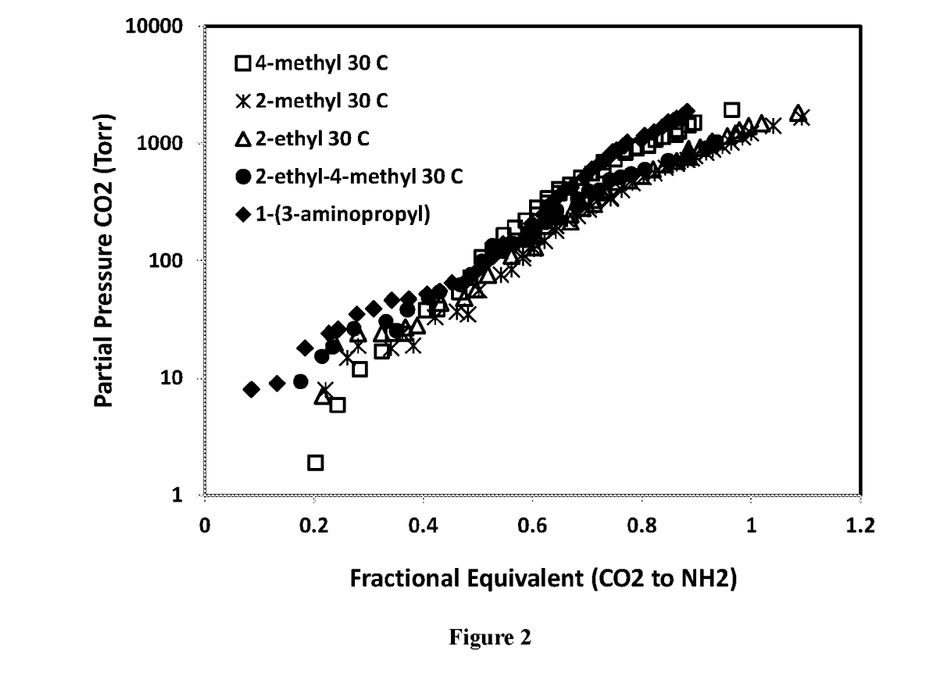
FIG. 2 is a graph of $CO_2$ uptake as a function of partial pressure of $CO_2$ for solutions containing 4-methyl-aminopropyl imidazole (4-methyl); 2-methyl-aminopropyl imidazole (2-methyl); 2-ethyl aminopropyl imidazole (2-ethyl); 2-ethyl-4-methyl aminopropyl imidazole (2-ethyl-4-methyl), and 1-(3-aminopropyl)imidazole, at 30° C.
Figure 3:
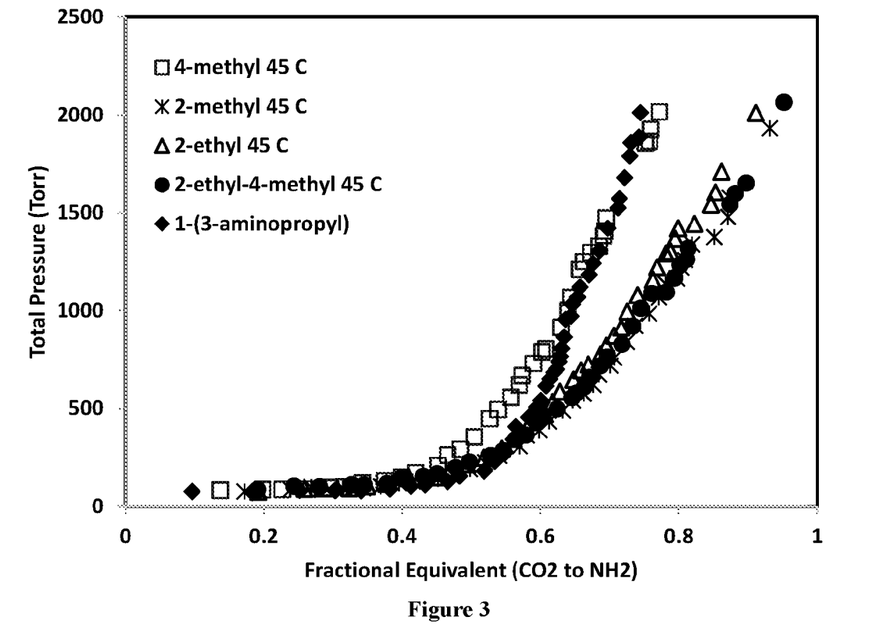
FIG. 3 is a graph of $CO_2$ uptake as a function of pressure for solutions containing 4-methyl-aminopropyl imidazole (4-methyl); 2-methyl-aminopropyl imidazole (2-methyl); 2-ethyl aminopropyl imidazole (2-ethyl); 2-ethyl-4-methyl aminopropyl imidazole (2-ethyl-4-methyl), and 1-(3-aminopropyl)imidazole, at 45° C.
Figure 4:
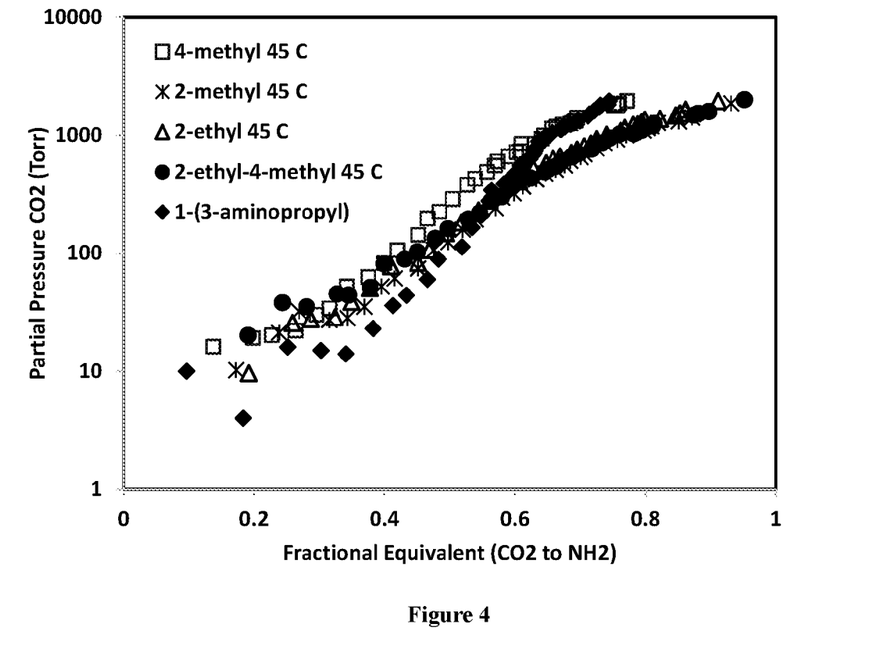
FIG. 4 is a graph of $CO_2$ uptake as a function of partial pressure of $CO_2$ for solutions containing 4-methyl-aminopropyl imidazole (4-methyl); 2-methyl-aminopropyl imidazole (2-methyl); 2-ethyl aminopropyl imidazole (2-ethyl); 2-ethyl-4-methyl aminopropyl imidazole (2-ethyl-4-methyl), and 1-(3-aminopropyl)imidazole, at 45° C.
Figure 5:
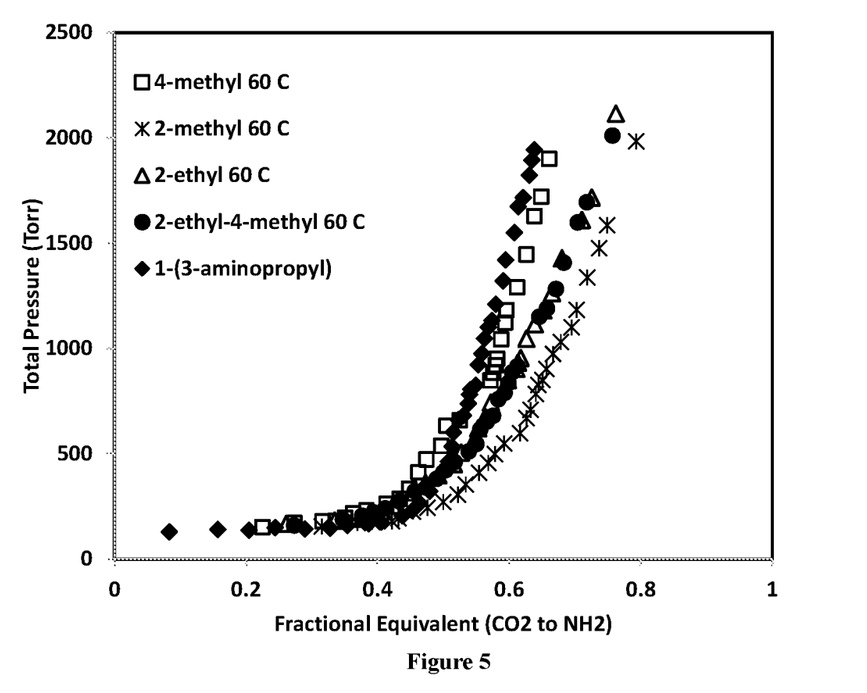
Figure 6:
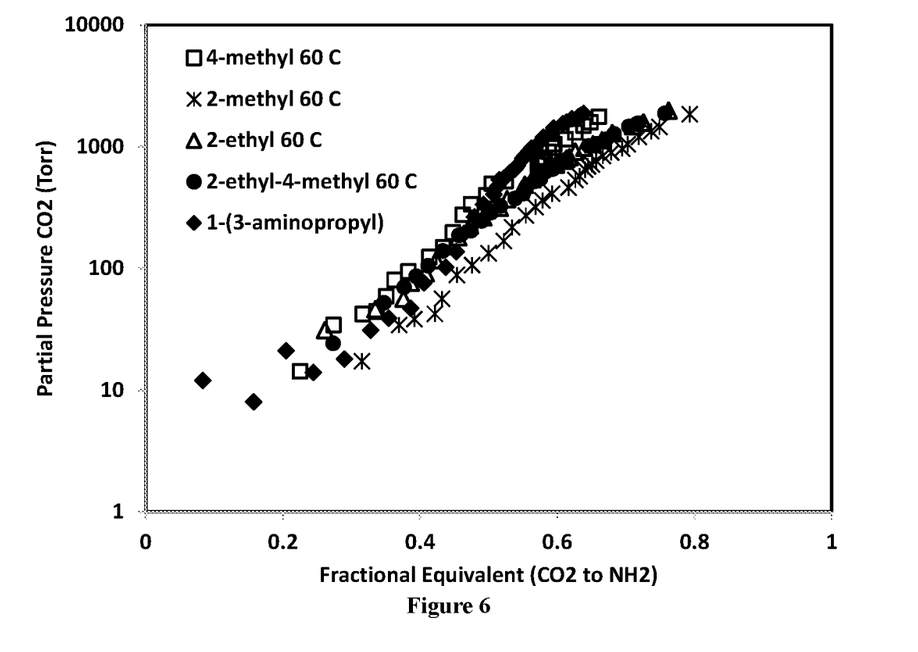
FIG. 6 is a graph of $CO_2$ uptake as a function of partial pressure of $CO_2$ for solutions containing 4-methyl-aminopropyl imidazole (4-methyl); 2-methyl-aminopropyl imidazole (2-methyl); 2-ethyl aminopropyl imidazole (2-ethyl); 2-ethyl-4-methyl aminopropyl imidazole (2-ethyl-4-methyl), and 1-(3-aminopropyl)imidazole, at 60° C.
Figure 7:
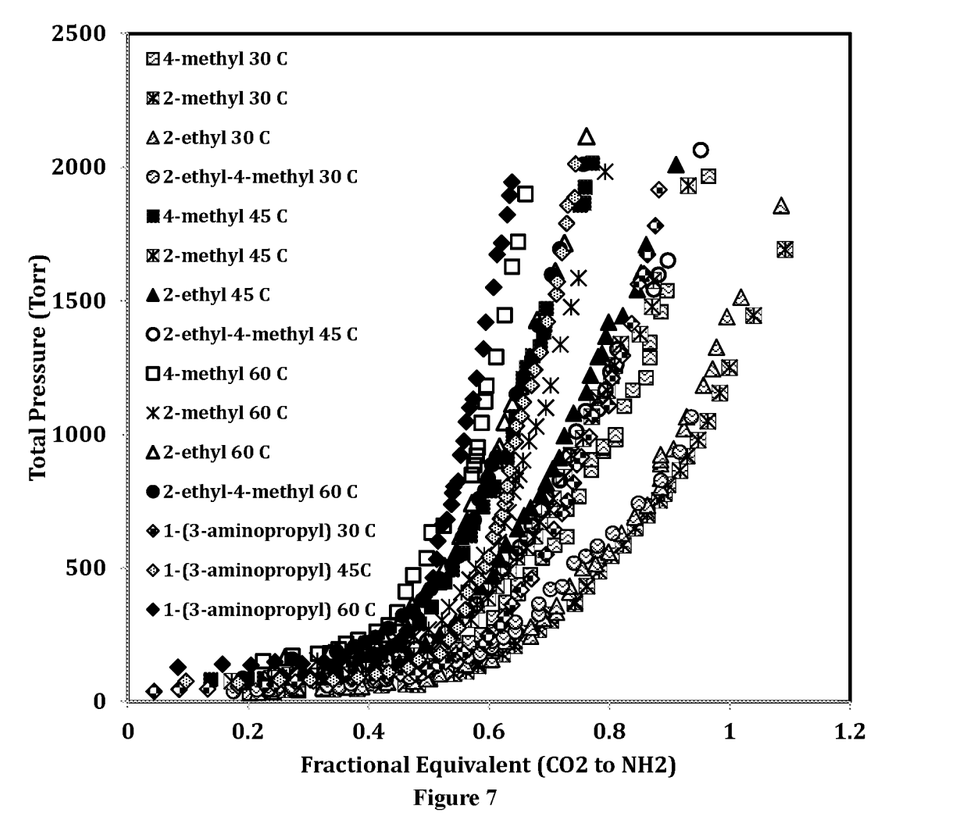
FIG. 7 is a graph comparing the $CO_2$ uptake as a function of pressure as shown in FIGS. 1, 3, and 5.

To assess the $CO_2$ uptake of the amine-functionalized imidazoles compared to 1-(3-aminopropyl)imidazole, the solutions were loaded into a sealed vessel of known volume, heated to 30° C., 45° C., or 60° C., and exposed to $CO_2$ at pressures ranging from 0 torr to 2000 torrs with stirring. As can be seen in FIGS. 1-7, the addition of the amine-functionalized imidazoles enhanced $CO_2$, uptake compared to uptake by 1-(3-aminopropyl)imidazole. The effect was particularly notable at a pressure of about 760 torr and greater. There was also an increase in $CO_2$ uptake as the temperature decreased from 60° C. to 30° C., for the amine-functionalized imidazoles.

What is claimed is:

1. A method for reducing volatile compounds from a stream, comprising:
   contacting the stream with a system comprising an imidazole tethered by a tether ("R") to an amine and a solvent, wherein the imidazole tethered to an amine does not include 1-(3-aminopropyl)imidazole (API) and is non-ionic under neutral conditions, and
   wherein the volatile compounds are selected from the group consisting of carbon dioxide, hydrogen sulfide, sulfur dioxide, nitrogen oxide, nitrogen dioxide, carbonyl sulfide, carbon disulfide, or mixtures thereof,
   wherein the imidazole tethered to an amine has the following structure:

wherein,
X, Y, and Z are, independent of one another, selected from the group consisting of hydrogen, halogen, hydroxyl, carbonyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, and substituted or unsubstituted heteroaryl; and wherein at least one of X, Y, and Z is unsubstituted $C_{1-4}$ alkyl, R is selected from the group consisting of substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, and substituted or unsubstituted heteroaryl; and $R^1$ and $R^2$ are, independent of one another, selected from the group consisting of hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, and substituted or unsubstituted aryloxyl.

2. The method of claim 1, wherein the solvent is selected from the group consisting of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, acetone, and mixtures thereof.

3. The method of claim 1, wherein the imidazole tethered to an amine is from 20 to 80 weight percent in solution.

4. The method of claim 1, wherein the solvent is water.

5. The method of claim 1, wherein the tether, R, is propyl (—$CH_2CH_2CH_2$—).

6. The method of claim 1, wherein the imidazole tethered to an amine is selected from the group consisting of

7. The method of claim 1, wherein the volatile compound is carbon dioxide.

8. A method for sweetening a natural gas feed stream, comprising:
contacting the natural gas feed stream with a system comprising an imidazole tethered by a tether ("R") to an amine, wherein the imidazole tethered to an amine does not include 1-(3-aminopropyl) imidazole (API) and is non-ionic under neutral conditions, and a solvent to form a purified natural gas feed stream and a gas-rich system;

and separating the purified natural gas feed stream from the gas-rich system, wherein natural gas feed stream comprises a volatile compound selected from the group consisting of carbon dioxide, hydrogen sulfide, sulfur dioxide, nitrogen oxide, nitrogen dioxide, carbonyl sulfide, carbon disulfide, or mixtures thereof, wherein the imidazole tethered to an amine has the following structure:

wherein,

X, Y, and Z are, independent of one another, selected from the group consisting of hydrogen, halogen, hydroxyl, carbonyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, and substituted or unsubstituted heteroaryl; and wherein at least one of X, Y, and Z is unsubstituted $C_{1-4}$ alkyl, R is selected from the group consisting of substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, and substituted or unsubstituted heteroaryl; and $R^1$ and $R^2$ are, independent of one another, selected from the group consisting of hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, and substituted or unsubstituted aryloxyl.

9. The method of claim 8, wherein the solvent is selected from the group consisting of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, acetone, and mixtures thereof.

10. The method of claim 8, wherein the imidazole tethered to an amine is from 20 to 80 weight percent in solution.

11. The method of claim 8, wherein the solvent is water.

12. The method of claim 8, wherein the tether, R, is propyl (—CH$_2$CH$_2$CH$_2$—).

13. The method of claim 8, wherein the imidazole tethered to an amine is selected from the group consisting of 14. A system for the reduction of volatile compounds, comprising:
an imidazole tethered by a tether ("R") to an amine, wherein the imidazole tethered to an amine does not include 1-(3-aminopropyl)imidazole (API) and is non-ionic under neutral conditions;
a solvent; and
a volatile compound selected from the group consisting of carbon dioxide, hydrogen sulfide, sulfur dioxide, nitrogen oxide, nitrogen dioxide, carbonyl sulfide, carbon disulfide, or mixtures thereof,
wherein the imidazole tethered to an amine has the following structure:

wherein,
X, Y, and Z are, independent of one another, selected from the group consisting of hydrogen, halogen, hydroxyl, carbonyl, substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted cycloalkyl, substituted or unsubstituted heterocycloalkyl, substituted or unsubstituted aryl, and substituted or unsubstituted heteroaryl; and wherein at least one of X, Y, and Z is unsubstituted C$_{1-4}$ alkyl,
R is selected from the group consisting of substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted cycloalkyl, substituted or unsubstituted heterocycloalkyl, substituted or unsubstituted aryl, and substituted or unsubstituted heteroaryl; and
R$^1$ and R$^2$ are, independent of one another, selected from the group consisting of hydrogen, substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{1-20}$ heteroalkyl, substituted or unsubstituted C$_{2-20}$ heteroalkenyl, substituted or unsubstituted C$_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, and substituted or unsubstituted aryloxyl.

15. The system of claim 14, wherein the solvent is selected from the group consisting of water, tetrahydrofuran, dichloromethane, acetonitrile, toluene, dimethyl sulfoxide, pyridine, dimethylformamide, dioxane, glycol solvents, methanol, ethanol, propanol, butanol, ethyl acetate, methyl ethyl ketone, acetone, and mixtures thereof.

16. The system of claim 14, wherein the imidazole tethered to an amine is from 20 to 80 weight percent in solution.

17. The system claim 14, wherein the solvent is water.

18. The system of claim 14, wherein the tether, R, is propyl (—CH$_2$CH$_2$CH$_2$—).

19. The system of claim 14, wherein the imidazole tethered to an amine is selected from the group consisting of 20. A system for the reduction of volatile compounds, comprising:
an imidazole tethered by a tether ("R") to an amine, wherein the imidazole tethered to an amine does not include 1-(3-aminopropyl)imidazole (API) and is non-ionic under neutral conditions;
a solvent; and
a volatile compound selected from the group consisting of carbon dioxide, hydrogen sulfide, sulfur dioxide, nitrogen oxide, nitrogen dioxide, carbonyl sulfide, carbon disulfide, or mixtures thereof,
wherein the tether, R, is propyl (—CH$_2$CH$_2$CH$_2$—).

* * * * *